United States Patent
Riley et al.

(10) Patent No.: US 9,486,579 B2
(45) Date of Patent: Nov. 8, 2016

(54) HIGH PRESSURE SENSOR FOR USE WITH A FLUID DELIVERY SYSTEM

(71) Applicant: MEDRAD, INC., Indianola, PA (US)

(72) Inventors: Michael A Riley, Saxonburg, PA (US); Michael A Spohn, Fenelton, PA (US); Gerald W Callan, Cranberry Township, PA (US); Michael J Swantner, Saxonburg, PA (US); Russell M Evans, III, Mars, PA (US)

(73) Assignee: Bayer HealthCare LLC, Whippany, NJ (US)

( * ) Notice: Subject to any disclaimer, the term of this patent is extended or adjusted under 35 U.S.C. 154(b) by 236 days.

(21) Appl. No.: 13/798,709

(22) Filed: Mar. 13, 2013

(65) Prior Publication Data

US 2013/0255390 A1    Oct. 3, 2013

Related U.S. Application Data

(60) Provisional application No. 61/619,600, filed on Apr. 3, 2012.

(51) Int. Cl.
*A61M 5/172* (2006.01)
*A61M 5/00* (2006.01)
(Continued)

(52) U.S. Cl.
CPC .......... *A61M 5/1723* (2013.01); *A61M 5/007* (2013.01); *A61M 5/16854* (2013.01);
(Continued)

(58) Field of Classification Search
CPC .................. A61M 5/1723; A61M 2205/3337; F16K 17/02

USPC ................ 73/723, 705, 861.47, 861.42, 715; 137/877
See application file for complete search history.

(56) References Cited

U.S. PATENT DOCUMENTS 4,331,262 A    5/1982    Snyder et al.
4,342,218 A    8/1982    Fox
(Continued)

FOREIGN PATENT DOCUMENTS

DE    202005015741    1/2006
EP    1602388    11/2009
(Continued)

OTHER PUBLICATIONS

Hemodynamic Monitoring: Principles to Practice—M. L. Cheatham, MD, FACS, FCCM, Revised on Jan. 13, 2009.*
(Continued)

*Primary Examiner* — Laura Martin
*Assistant Examiner* — Suman K Nath
(74) *Attorney, Agent, or Firm* — Joseph L. Kent; David Schramm; James R. Stevenson

(57) ABSTRACT

A pressure sensor for use with a fluid delivery system having good sensitivity at low pressure, but also configured to remain in operating condition after being exposed to high pressures is disclosed herein. In one variation, the pressure sensor includes a fluid path set, a deformable element associated with the fluid path set and configured to deform in response to an external pressure, and a pressure transducer for monitoring deformation of the deformable element. In certain embodiments, the pressure sensor is configured to measure fluid pressure within the range of between about 0 mm Hg to about 300 mm Hg. However, the sensor pressure is also be configured to remain functional after being exposed to pressure in excess of about 60,000 mm Hg.

30 Claims, 10 Drawing Sheets

(51) Int. Cl.
*A61M 5/168* (2006.01)
*G01L 19/06* (2006.01)
*G01L 11/02* (2006.01)

(52) U.S. Cl.
CPC ........ *G01L 11/025* (2013.01); *G01L 19/0618* (2013.01); *A61M 2205/3337* (2013.01); *A61M 2205/3355* (2013.01)

(56) References Cited

U.S. PATENT DOCUMENTS

| | | | |
|---|---|---|---|
| 4,384,470 A | 5/1983 | Fiore | |
| 4,610,256 A | 9/1986 | Wallace | |
| 4,815,313 A | 3/1989 | Beard | |
| 5,140,862 A | 8/1992 | Pappalardo | |
| 5,174,038 A | 12/1992 | Neyens et al. | |
| 5,263,367 A | 11/1993 | Pippert | |
| 5,460,609 A | 10/1995 | O'Donnell | |
| 5,540,668 A | 7/1996 | Wilson, Jr. et al. | |
| 5,551,301 A * | 9/1996 | Cowan | 73/708 |
| 5,573,515 A | 11/1996 | Wilson et al. | |
| 5,630,935 A | 5/1997 | Treu | |
| 5,631,552 A | 5/1997 | Ogawa et al. | |
| 5,684,246 A | 11/1997 | Korpi | |
| 5,800,397 A | 9/1998 | Wilson et al. | |
| 5,808,203 A | 9/1998 | Nolan, Jr. et al. | |
| 5,967,176 A * | 10/1999 | Blann et al. | 137/489.5 |
| 6,171,253 B1 * | 1/2001 | Bullister et al. | 600/486 |
| 6,422,057 B1 | 7/2002 | Anderson | |
| 6,650,929 B1 | 11/2003 | Nemoto et al. | |
| 7,094,216 B2 | 8/2006 | Trombley, III et al. | |
| 7,291,131 B2 | 11/2007 | Call | |
| 7,389,788 B2 * | 6/2008 | Wilson | A61B 5/0215 137/112 |
| 7,556,619 B2 | 7/2009 | Spohn et al. | |
| 7,610,936 B2 * | 11/2009 | Spohn et al. | 137/877 |
| 7,713,239 B2 | 5/2010 | Uber, III et al. | |
| 8,147,464 B2 | 4/2012 | Spohn et al. | |
| 8,337,456 B2 | 12/2012 | Schriver et al. | |
| 8,361,040 B2 | 1/2013 | Spohn et al. | |
| 2002/0016569 A1 | 2/2002 | Critchlow et al. | |
| 2003/0171712 A1 | 9/2003 | Critchlow et al. | |
| 2004/0064041 A1 | 4/2004 | Lazzaro et al. | |
| 2004/0143225 A1* | 7/2004 | Callan et al. | 604/247 |
| 2004/0221904 A1 | 11/2004 | Usher et al. | |
| 2005/0113754 A1 | 5/2005 | Cowan | |
| 2005/0234428 A1 | 10/2005 | Spohn et al. | |
| 2006/0009699 A1* | 1/2006 | Roteliuk et al. | 600/486 |
| 2006/0079765 A1 | 4/2006 | Neer et al. | |
| 2006/0180202 A1 | 8/2006 | Wilson et al. | |
| 2008/0045919 A1 | 2/2008 | Jakob et al. | |
| 2008/0086087 A1 | 4/2008 | Spohn et al. | |
| 2008/0154214 A1 | 6/2008 | Spohn et al. | |
| 2009/0216192 A1 | 8/2009 | Schriver et al. | |
| 2012/0123257 A1 | 5/2012 | Stokes, Jr. et al. | |
| 2013/0123619 A1* | 5/2013 | Griggs | A61M 5/007 600/432 |
| 2013/0197883 A1 | 8/2013 | Grow et al. | |
| 2014/0034169 A1 | 2/2014 | Harton et al. | |

FOREIGN PATENT DOCUMENTS

| | | | |
|---|---|---|---|
| EP | 1602388 B1 | 11/2009 | |
| WO | 9308454 A1 | 4/1993 | |
| WO | 9422686 | 10/1994 | |
| WO | WO 9422686 A1 * | 10/1994 | B60K 28/06 |
| WO | 9522280 | 8/1995 | |
| WO | WO 9522280 A1 * | 8/1995 | A61B 5/02 |
| WO | 0065984 | 11/2000 | |
| WO | 2011041290 | 4/2011 | |
| WO | 2012155035 | 11/2012 | |

OTHER PUBLICATIONS

Hemohynamic Monitoring: Principles to Practice—M. L. Cheatham, MD, FACS, FCCM, Revised on Jan. 13, 2009.*
OMRON Instruction Manual, 7 series, Blood Pressure Monitor with ComFit Cuff, 2010.*
The International Preliminary Report on Patentability of corresponding PCT Application No. PCT/US2013/034896.
The Notification of Transmittal of the ISR and the Written Opinion of the International Searching Authority in the corresponding PCT Application No. PCT/US2013/034896 filed on Apr. 2, 2013.
Cheatham. Hemodynamic Monitoring: Principles to Practice. Surgical Crital Care Lecture. Jan. 13, 2009.
Omron. 7 Series Blook Pressure Monitor with ComFit Cuff. Instruction Manual. 2010.
The Final Office Action mailed on Jul. 31, 2015 from related U.S. Appl. No. 13/755,883.
The Supplementary European Search Report dated Oct. 29, 2015 from corresponding EP Application No. EP13772495.
The Non-Final Office Action dated Mar. 18, 2015 from related U.S. Appl. No. 13/755,883, filed Jan. 31, 2013.
The International Preliminary Report on Patentability from corresponding PCT Application No. PCT/US2013/064938 dated on Apr. 30, 2015.
The Non-Final Office Action dated Mar. 4, 2015 from related U.S. Appl. No. 13/798,709, filed Mar. 13, 2013.
The International Search Report and Written Opinion of corresponding PCT Application No. PCT/US2013/064938 dated on Feb. 3, 2014.

* cited by examiner

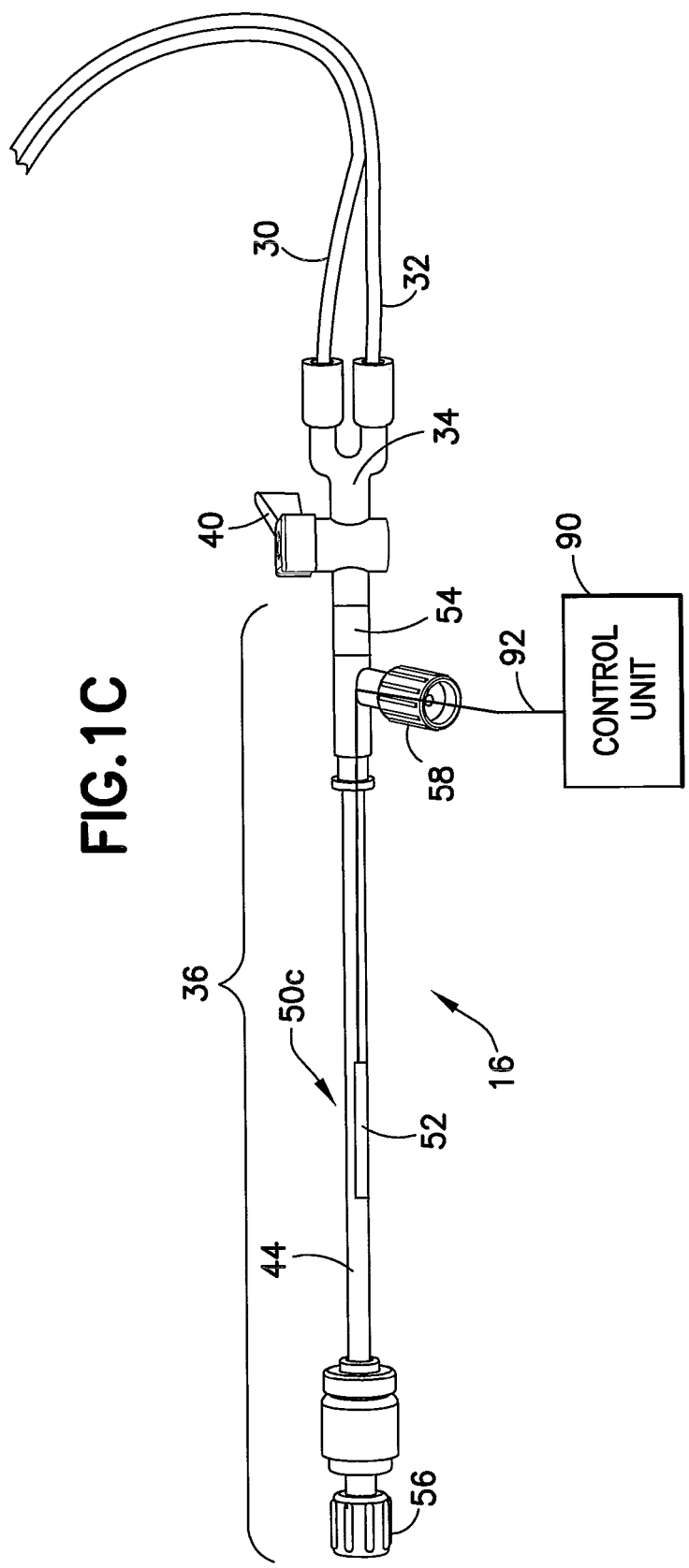

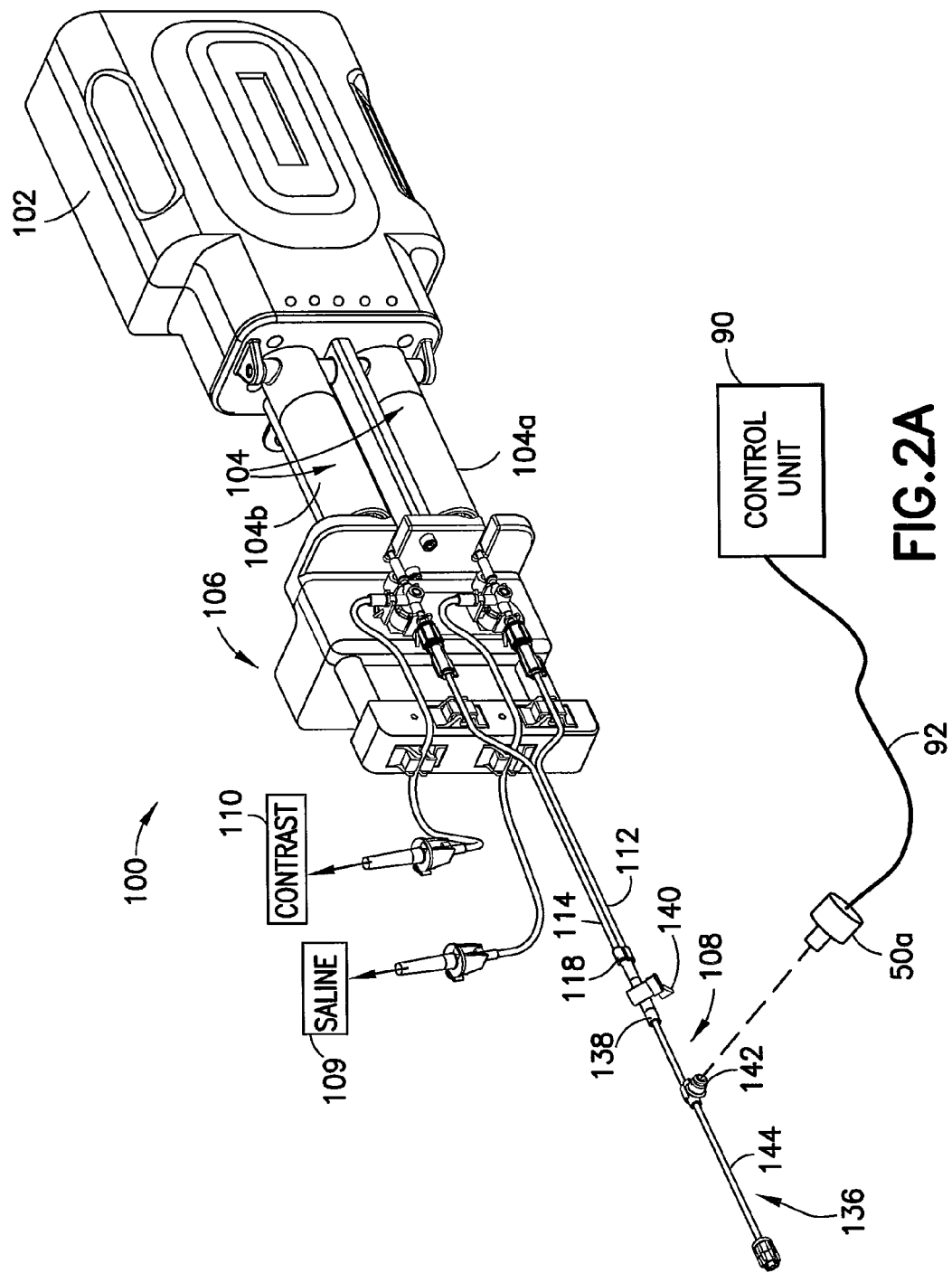

HIGH PRESSURE SENSOR FOR USE WITH A FLUID DELIVERY SYSTEM

CROSS REFERENCE TO RELATED APPLICATION

This application claims the benefit of U.S. Provisional Application No. 61/619,600, filed Apr. 3, 2012, entitled "High Pressure Transducer", which is hereby incorporated by reference in its entirety.

BACKGROUND OF THE INVENTION

1. Field of the Invention

The disclosure relates generally to medical fluid delivery applications and, particularly, to a fluid delivery system including a high pressure sensor for measuring intravascular pressure of a patient during medical fluid delivery applications.

2. Description of Related Art

In many medical diagnostic and therapeutic procedures, a medical practitioner, such as a physician, injects a patient with a fluid. In recent years, a number of injector-actuated syringes and powered fluid injectors for pressurized injection of fluids, such as contrast media (often referred to simply as "contrast"), have been developed for use in procedures such as angiography, computed tomography, ultrasound, and NMR/MRI. In general, these powered fluid injectors are designed to deliver a preset amount of contrast at a preset flow rate.

Angiography is used in the detection and treatment of abnormalities or restrictions in blood vessels. In an angiographic procedure, a radiographic image of a vascular structure is obtained through the use of a radiographic contrast that is injected through a catheter. The vascular structures in fluid connection with the vein or artery in which the contrast is injected are filled with contrast. X-rays passing through the region of interest are absorbed by the contrast, causing a radiographic outline or image of blood vessels containing the contrast. The resulting images can be displayed on, for example, a video monitor and recorded.

In a typical angiographic procedure, the medical practitioner places a cardiac catheter into a vein or artery. The catheter is connected to either a manual or an automatic contrast injection mechanism. A typical manual contrast injection mechanism includes a syringe in fluid connection with a catheter connection. The fluid path also includes, for example, a source of contrast, a source of flushing fluid, typically saline, and a pressure transducer to measure patient blood pressure. In a typical system, the source of contrast is connected to the fluid path via a valve, for example, a three-way stopcock. The source of saline and the pressure transducer may also be connected to the fluid path via additional valves, again, such as stopcocks. The operator of the manual contrast injection mechanism controls the syringe and each of the valves to draw saline or contrast into the syringe and to inject the contrast or saline into the patient through the catheter connection. The operator of the syringe may adjust the flow rate and volume of injection by altering the force applied to the plunger of the syringe. Thus, manual sources of fluid pressure and flow used in medical applications, such as syringes and manifolds, typically require operator effort that provides feedback of the fluid pressure/flow generated to the operator. The feedback is desirable, but the operator effort often leads to fatigue. Thus, fluid pressure and flow may vary depending on the operator's strength and technique.

Automatic contrast injection mechanisms typically include a syringe connected to a powered fluid injector having, for example, a powered linear actuator. Typically, an operator enters settings into an electronic control system of the powered fluid injector for a fixed volume of contrast and a fixed rate of injection. In many systems, there is no interactive control between the operator and the powered fluid injector, except to start or stop the injection. A change in flow rate in such systems occurs by stopping the machine and resetting the injection parameters. Automation of angiographic procedures using powered fluid injectors is discussed, for example, in U.S. Pat. Nos. 5,460,609; 5,573,515; and 5,800,397.

The pressure transducer in the above-discussed modalities is used to provide a hemodynamic waveform, referred to as intra-coronary blood pressure, of a patient during clinical procedures. Cardiologists often refer to hemodynamic waveforms since they essentially provide real time measurement of blood pressure, which correlates to the performance of the heart. However, these pressure transducers are extremely sensitive to even moderate pressures generated during activation of the syringe, and many pressure transducers can be damaged if they are subjected to pressures as low as about 75 psi. Hand-held syringes can generate pressures of 200 psi or more. Power injectors may pressurize the contents of a syringe to pressure exceeding 1200 psi (about 63,000 mm Hg), far beyond the maximum pressure of the pressure transducer.

In view of these high pressure levels in existing fluid delivery systems, the systems include a means, such as a valve, for isolating the pressure transducer from the pressurized fluid in order to avoid damaging the pressure transducer during injection. While the syringe is not activated, the valve is open so that the pressure transducer can monitor blood pressure. In one known arrangement, the pressure transducer and contrast injection mechanism are connected to the catheter through a manifold. The manifold includes a manually operated valve that enables the injector operator to isolate the pressure transducer during the injection of the contrast solution. This valve, typically a stopcock, is used to isolate the pressure transducer to prevent damage thereto. Specifically, a stopcock configuration is provided which either allows the pressure transducer to be in fluid communication with the catheter or the injection mechanism to be in fluid communication with the catheter, but not both. Typically, the stopcock handle must be turned manually to switch between the two positions. Accordingly, this configuration provided by some currently available manifolds does not allow, for example, contrast injections to be made while the pressure transducer is in communication with the catheter.

Another pressure isolation valve used for pressure transducer protection purposes is disclosed by U.S. Patent Application Publication No. 2006/0180202 to Wilson, et al. This publication discloses an elastomeric valve having a valve body with three ports including a contrast inlet port, a saline inlet and pressure transducer port, and a patient or outlet port. The valve body houses a disc holder and a valve disc therein. The valve disc is formed from a molded elastomer, such as silicone rubber, with a slit in the center. The elastomeric disc is sandwiched between the valve body and disc holder and is affixed therebetween at the perimeter of the disc. Such affixation may be effected by entrapment, adhesion, mechanical, or chemical welding. The elastomeric valve disclosed by this publication is responsive to pressure changes in the valve that act on the elastomeric disc, and the elastomeric disc is operative to protect a pressure transducer connected to the pressure isolation port.

Fluid delivery systems having pressure isolation valves that open and close automatically are also known in the art. For example, U.S. Pat. No. 7,610,936 to Spohn, et al., incorporated herein by reference, discloses a fluid delivery system having a pressure isolation mechanism that includes a flow-activated valve member adapted to selectively engage a seal seat to establish fluid isolation between a fluid delivery system and a pressure transducer. The flow-activated valve member is responsive to increased fluid flow through a fluid path connected to the pressure isolation mechanism and the valve member is operable to engage and seal against an opposing seal seat. The valve member movement effectively closes-off fluid flow to a port to which a pressure transducer is connected, thereby isolating the pressure transducer when high pressure fluid is injected through the fluid path.

However, despite the fact the above-described valves effectively protect and isolate a pressure transducer when used correctly, there are a number of drawbacks to such active pressure isolation valve mechanisms. First, with manual isolation valves, the user may forget to close the valve before activating the associated syringe, and the pressurized fluid flow through the system will likely damage the transducer. Additionally, if the valve is not closed correctly, there is a risk that fluid drainage would occur through the valve or port, during pressure transducer zeroing. Furthermore, automatic or active pressure isolation valves often rely on sealing, locking, or release mechanisms which tend to be complex and, in some cases, prone to breaking or becoming stuck in an open or closed position, or have a tendency to trap air.

Additionally, known pressure sensors must be positioned in a separate port, typically a branch port, a secondary fluid path, or line from the main fluid path of a fluid delivery system. While the branch port or the secondary fluid path is selectively in fluid communication with the main fluid path, the branch or delta between the pressure sensor and the main fluid path reduces the accuracy and reliability of pressure measurements. Furthermore, each branch of a fluid system must be primed with a fluid, such as saline, during use. In systems in which the pressure sensor is included in a branch, port, or secondary fluid path, which is separate from the main fluid path, a user must perform an extra flushing activity on the branch, port, or secondary fluid path leading to the pressure sensor, and these locations are prime locations for trapping air bubbles. Performing an additional flushing activity increases the difficulty and time required to perform a fluid injection.

SUMMARY OF THE INVENTION

Therefore, in view of the foregoing, there is a need for applying a pressure sensor to a fluid injection system without the need for active pressure isolation mechanisms. For example, it would be beneficial if the pressure transducer of the pressure sensor remained in continuous fluid communication with the fluid path between the fluid delivery system and the patient, without the risk that pressurized fluid would damage the pressure transducer. However, the pressure transducer should also be capable of measuring small changes in pressure to provide useful information about intravascular blood pressure, particularly in the range of about 0 mm Hg to about 300 mm Hg. It would also be beneficial if the pressure transducer were configured to reduce fluid drainage during zeroing and to simplify the process of priming the fluid delivery system during use. The pressure transducer and fluid delivery system detailed herein provide such beneficial characteristics.

A pressure sensor for use with a fluid delivery system having good sensitivity at low pressure but also configured to remain in operating condition after being exposed to high pressures is disclosed in detail herein. In one embodiment, a hemodynamic pressure sensor for use with a fluid delivery system is disclosed, comprising a fluid path defined by a tubing element, and a pressure transducer in continuous fluid communication with fluid in the tubing element and adapted to measure fluid pressure in the tubing element. Fluid communication may mean direct contact with a fluid medium or indirect, for example, across a membrane or other barrier to permit the pressure transducer to ascertain fluid pressure readings in the tubing element. The pressure transducer comprises a deformable element configured to deform in response to changing fluid pressure in the tubing element. The pressure transducer converts to an electronic signal a representation of the amount of deformation of the deformable element to measure the changing fluid pressure in the tubing element.

The pressure transducer may be configured to measure pressure within the range of between about 0 mm Hg to about 300 mm Hg, and the pressure transducer may be configured such that it remains in working condition after being exposed to pressure in excess of about 60,000 mm Hg.

The pressure transducer may be configured to be placed in fluid connection with a pressure port in fluid communication with the tubing element.

The pressure transducer may be an optical pressure transducer and the deformable element may be a flexible tube enclosing the optical pressure transducer. The pressure transducer may further comprise a radiation generator for promulgating a radiation beam through the flexible tube and a detector for detecting the promulgated radiation beam. The flexible tube may be configured to deform in response to fluid pressure in the tubing element, and the pressure transducer may be configured to measure the deformation of the flexible tube.

The deformable element may be a diaphragm which flexes in response to changing fluid pressure within the tubing element, and the pressure transducer may measure flexing of the diaphragm and convert to an electronic signal a representation of the amount of flexing of the diaphragm to measure the changing fluid pressure in the tubing element. A guard may be provided to selectively engage and restrict movement of the diaphragm. The guard may engage the diaphragm when fluid pressure in the tubing element exceeds a possible human intra-coronary pressure range.

An external monitor may be in electronic communication with the pressure transducer. The external monitor may comprise a signal analysis processor for receiving the electronic signal from the pressure transducer and be adapted to process the electronic signal and transmit the electronic signal to a control unit.

A visual display may be provided on the external monitor for displaying the electronic signal for a user. The visual display may comprise a visual indicator comprising at least a warning indicator which informs the user when measured fluid pressure is outside of a possible human range of intracoronary pressure; a caution indicator that informs the user when measured pressure is outside of a normal human range for intracoronary pressure, but within the possible human range; and a ready-for-use indicator that indicates that measured fluid pressure is within the normal human range.

The pressure transducer may be connected to an external monitor by one of a wired and wireless connection.

Another embodiment is directed to a fluid delivery system comprising a first pressure fluid delivery device for delivering a first injection fluid under pressure to a fluid path defined by a tubing element, a second pressure fluid delivery device for delivering a second injection fluid under pressure to the tubing element and a pressure transducer in continuous fluid communication with fluid in the tubing element and adapted to measure fluid pressure in the tubing element. Fluid communication may mean direct contact with a fluid medium or indirect, for example, across a membrane or other barrier to permit the pressure transducer to ascertain fluid pressure readings in the tubing element. The pressure transducer comprises a deformable element configured to deform in response to changing fluid pressure in the tubing element. The pressure transducer converts to an electronic signal a representation of the amount of deformation of the deformable element to measure the changing fluid pressure in the tubing element.

The fluid delivery system may further comprise a hand manifold comprising a plurality of fluid control valves in series fluid communication and connected to the fluid delivery devices and to the tubing element. The fluid control valves selectively permit fluid flow between the fluid delivery devices and the tubing element.

The pressure transducer may be configured to be placed in fluid connection with a pressure port in fluid communication with the tubing element.

The pressure transducer may be an optical pressure transducer and the deformable element may be a flexible tube enclosing the optical pressure transducer. The pressure transducer may further comprise a radiation generator for promulgating a radiation beam through the flexible tube and a detector for detecting the promulgated radiation beam. The flexible tube may be configured to deform in response to fluid pressure in the tubing element, and the pressure transducer may be configured to measure the deformation of the flexible tube.

The deformable element may be a diaphragm which flexes in response to changing fluid pressure within the tubing element, and the pressure transducer may measure flexing of the diaphragm and convert to an electronic signal a representation of the amount of flexing of the diaphragm to measure the changing fluid pressure in the tubing element. A guard may be provided to selectively engage and restrict movement of the diaphragm. An external monitor may be in electronic communication with the pressure transducer, and the external monitor may comprise a signal analysis processor for receiving the electronic signal from the pressure transducer. The external monitor may be adapted to process the electronic signal and transmit the electronic signal to a control unit.

A further embodiment is directed to a fluid delivery system comprising a power injector adapted to interface with and actuate at least one syringe, a fluid path set connected to the at least one syringe and comprising a tubing element, and a pressure transducer in continuous fluid communication with fluid in the tubing element and adapted to measure fluid pressure in the tubing element. Fluid communication may mean direct contact with a fluid medium or indirect, for example, across a membrane or other barrier to permit the pressure transducer to ascertain fluid pressure readings in the tubing element. The pressure transducer comprises a deformable element configured to deform in response to changing fluid pressure in the tubing element. The pressure transducer converts to an electronic signal a representation of the amount of deformation of the deformable element to measure the changing fluid pressure in the tubing element.

The pressure transducer may be configured to measure pressure within the range of between about 0 mm Hg to about 300 mm Hg, and the pressure transducer may be further configured such that it remains in working condition after being exposed to pressure in excess of about 60,000 mm Hg.

The pressure transducer may be configured to be placed in fluid connection with a pressure port in fluid communication with the tubing element.

The pressure transducer may be an optical pressure transducer and the deformable element may be a flexible tube enclosing the optical pressure transducer. The pressure transducer may further comprise a radiation generator for promulgating a radiation beam through the flexible tube, and a detector for detecting the promulgated radiation beam. The flexible tube may be configured to deform in response to fluid pressure in the tubing element, and the pressure transducer may be configured to measure the deformation of the flexible tube.

The deformable element may be a diaphragm which flexes in response to changing fluid pressure within the tubing element, and the pressure transducer may measure flexing of the diaphragm and convert to an electronic signal a representation of the amount of flexing of the diaphragm to measure the changing fluid pressure in the tubing element. A guard may be provided to selectively engage and restrict movement of the diaphragm.

An external monitor may be in electronic communication with the pressure transducer. The external monitor may comprise a signal analysis processor for receiving the electronic signal from the pressure transducer and be adapted to process the electronic signal and transmit the electronic signal to a control unit. A visual display may be provided on the external monitor for displaying the electronic signal for a user.

BRIEF DESCRIPTION OF THE DRAWINGS

For the purpose of facilitating understanding of this disclosure, the accompanying drawings and description illustrate certain embodiments, from which the various discussed structures, construction, method of operation, and many advantages provided by this disclosure may be understood and appreciated.

FIG. 1C is a perspective view of a fluid delivery system with a hardwired pressure sensor according to a further embodiment.

FIG. 2A is a perspective view of a fluid delivery system with a removable pressure sensor according to one embodiment.

DESCRIPTION OF THE PREFERRED EMBODIMENTS

For purposes of the description hereinafter, spatial orientation terms, as used, shall relate to the referenced embodiment as it is oriented in the accompanying drawing figures or otherwise described in the following detailed description. However, it is to be understood that the embodiments described hereinafter may assume many alternative variations and configurations. It is also to be understood that the specific components, devices, and features illustrated in the accompanying drawings and described herein are simply exemplary and should not be considered as limiting.

Figure 1A:
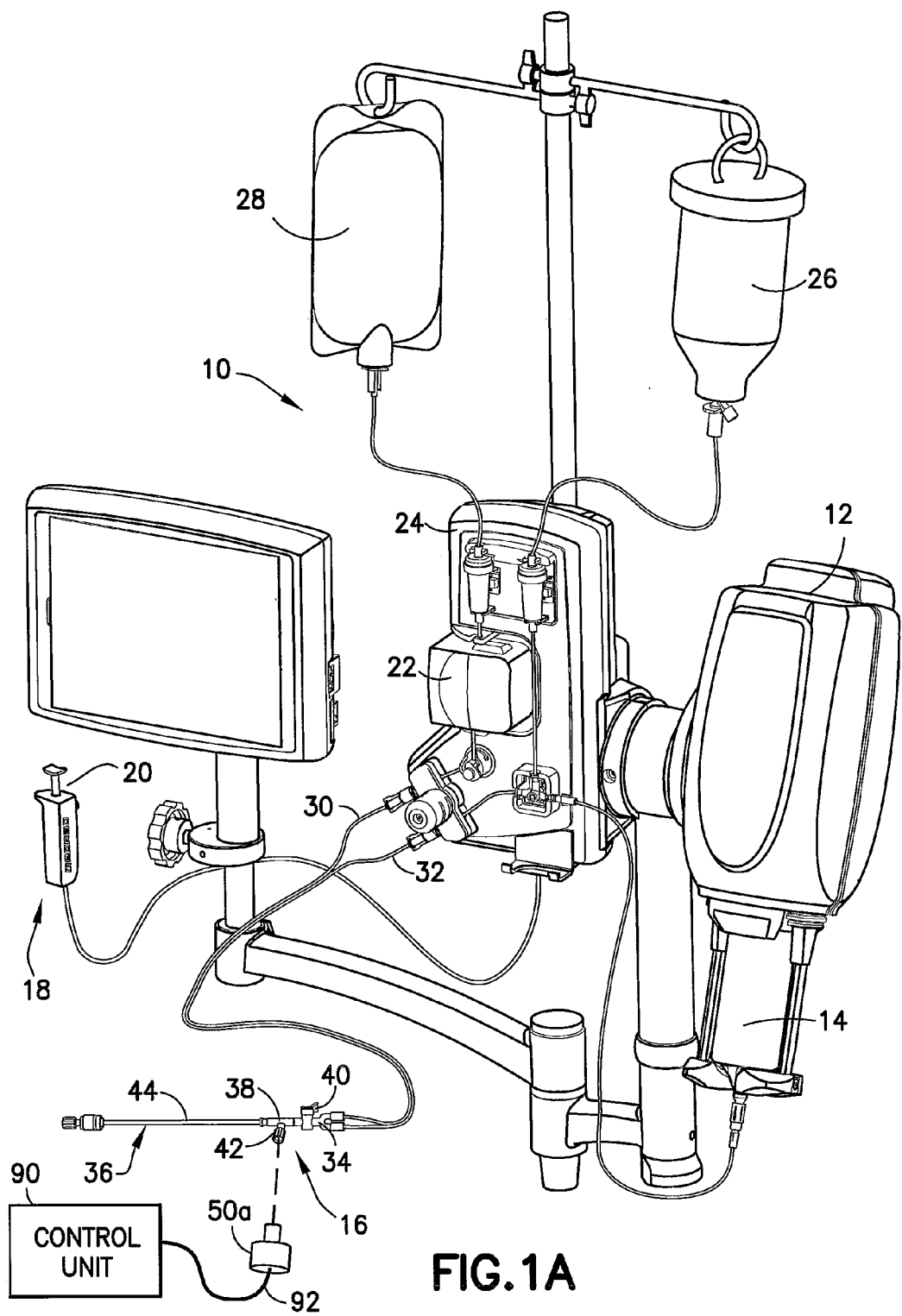
FIG. 1A is a perspective view of a fluid delivery system with a removable pressure sensor according to one embodiment.
Figure 1B:
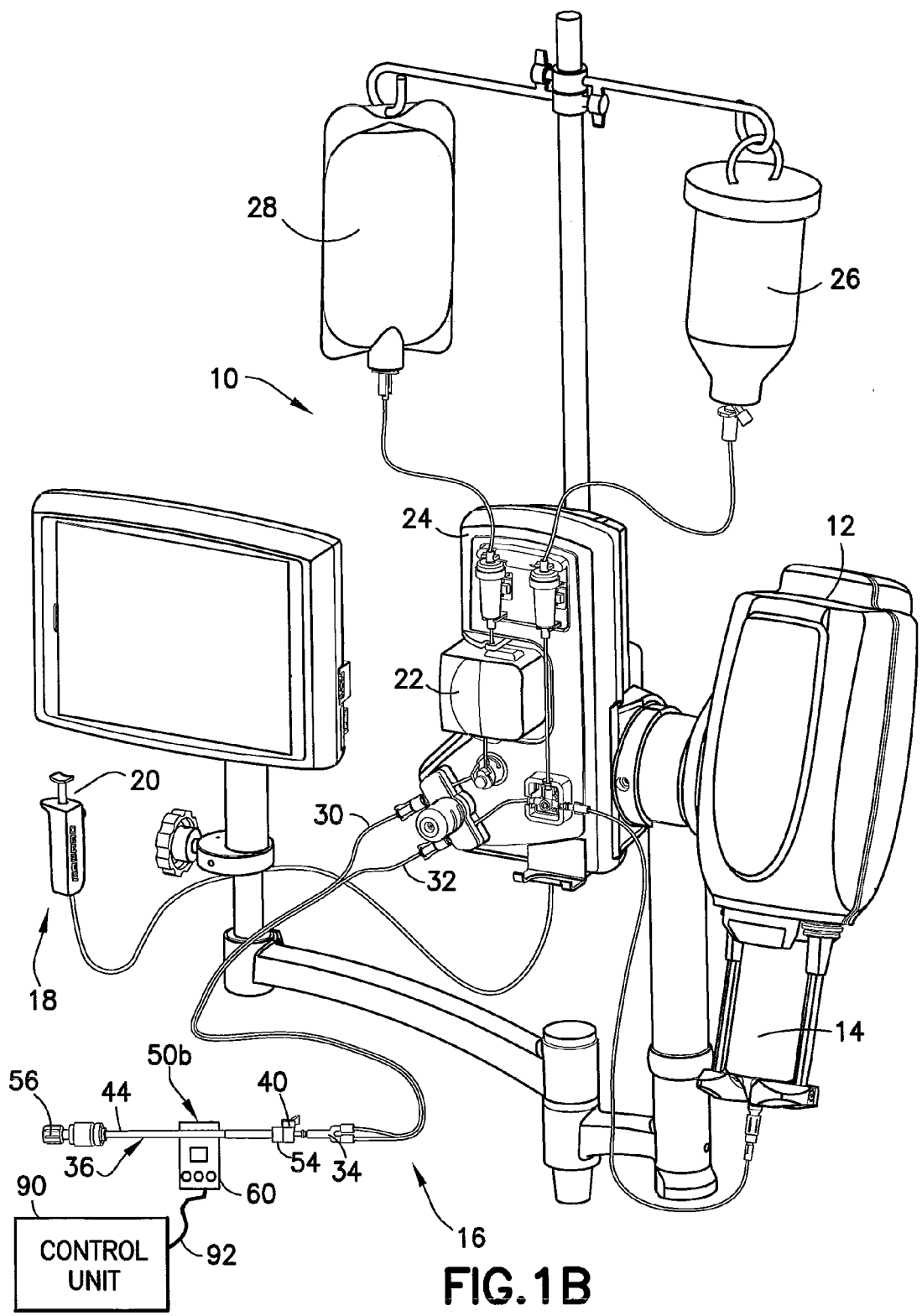
FIG. 1B is a perspective view of a fluid delivery system with a pressure sensor associated with a fluid path set according to another embodiment.

FIGS. 1A-1C are perspective views of an exemplary embodiment of a fluid delivery system 10. The fluid delivery system 10 is used to deliver fluids to a patient during a medical injection procedure. For example, the fluid delivery system 10 may be used during an angiographic procedure to inject contrast media and common flushing agents, such as saline, into the body of a patient. Details of the fluid injection or delivery system 10 are disclosed in U.S. patent application Ser. No. 09/982,518, filed on Oct. 18, 2001, now issued as U.S. Pat. No. 7,094,216 on Aug. 22, 2006 (hereinafter "the '216 patent"), and is assigned to the assignee of the present application, the disclosure of which is incorporated herein by reference in its entirety. Additional examples of fluid delivery systems are disclosed in the following references: U.S. patent application Ser. No. 10/825,866, filed on Apr. 16, 2004, now issued U.S. Pat. No. 7,556,619 on Jul. 7, 2009 (hereinafter "the '619 patent"); U.S. Pat. No. 8,337,456 to Schriver et al., issued Dec. 25, 2012; U.S. Pat. No. 8,147,464 to Spohn et al., issued Apr. 3, 2012; and, U.S. patent application Ser. No. 11/004,670, now published as U.S. 2008/0086087 on Apr. 10, 2008, each of which are assigned to the assignee of the present application and the disclosures of which are incorporated herein by reference in their entireties.

The fluid delivery system 10 generally includes a powered fluid injector 12 that is adapted to support and actuate a syringe 14 storing a first injection fluid for injection into a patient during a medical procedure, such as an angiographic procedure. The fluid injector 12 is generally used to supply the contrast media in the syringe 14 under pressure to a fluid path set 16 and, ultimately, a patient. The fluid injector 12 is optionally controlled by a hand controller 18 to supply the contrast media at discrete and preselected flow rates based on a physical input such as a trigger plunger 20. The fluid delivery system 10 further includes a second injection fluid that may be mixed with the first injection fluid prior to being delivered to a patient or delivered directly to the patient without mixing, depending on the mode of operation of the fluid injector 12. The second fluid is advanced by a pumping mechanism 22 such as a peristaltic pump. The powered fluid injector 12 is operatively associated with a fluid control module 24. The fluid control module 24 is generally adapted to support at least portions of the fluid path set 16. The fluid path set 16 is adapted to fluidly connect the syringe 14 to a source of contrast media 26 and a source of saline 28, which is supplied to the patient via the same catheter as the contrast media 26.

The fluid path set 16 may have single and multi-use disposable sections and includes a first input line 30 in selective fluid communication with the syringe 14, a second input line 32 in selective fluid communication with the source of saline 28, a downstream Y-connector 34 joining the first and second input lines 30, 32, and a catheter connector conduit 36. Additional aspects of the fluid path set 16 may be found in the '216 patent and the '619 patent referenced above. The catheter connector conduit 36 is a disposable tubing section that connects the fluid path set 16 to a catheter (not shown) that is inserted within a patient for supplying the contrast media 26 and saline 28 to the patient. Desirably, the catheter connector conduit 36 is removably connected by a suitable connector 38 to a stopcock valve 40 that is provided between the Y-connector 34 and the catheter connector conduit 36. The stopcock valve 40 may form a break point between reusable components of the fluid path set 16 and the disposable, single-use catheter connector conduit 36 in one embodiment. The stopcock valve 40 permits a user to isolate the reusable upstream components of the fluid path set 16 so that, when the stopcock valve 40 is in a closed position, a user can remove and replace the catheter connector conduit 36, and so that the multi-patient section of the fluid delivery system 10 can be used by another patient. The stopcock 40 is merely an exemplary structure for isolating the upstream components from the catheter connector conduit 36 and may be replaced by any suitable aseptic connector structure, but the stopcock 40 has the advantage of being manually actuated.

With specific reference to FIG. 1A, the fluid path set 16 may be configured with a pressure port 42, for example formed as a port on the connector 38 adapted for connection with the stopcock valve 40. A pressure sensor 50a according to one embodiment is configured to be removably coupled with the pressure port 42. It is desirable to position the pressure port 42 and the associated pressure sensor 50a as close to the catheter (not shown) as possible and, more specifically, to the patient to reduce the possibility that a pressure drop through the catheter and the catheter connector conduit 36 will reduce the reliability and accuracy of pressure measurements. The pressure sensor 50a is generally adapted to measure hemodynamic waves in tubing portion 44 of the catheter connector conduit 36. The hemodynamic waves provide an indication of intra-vascular blood pressure. The measured blood pressure is used, for example, to determine the location of a catheter within an access vein, artery, or heart chamber. More particularly, different areas of the heart and surrounding vasculature have different pressures. Therefore, monitoring intra-coronary pressure provides an effective way to identify the coronary area (e.g., the right atrium, right ventricle, pulmonary artery, left ventricle, or aortic root) where the catheter is located. The pressure in the fluid access line also provides a useful indication of whether the fluid path is ready for injection. Further, intravascular pressure can also be used for thrombosis detection. More specifically, the quality of the hemodynamic signal decays as the blood begins to clot. Therefore, as the catheter approaches the clotting area, a user will observe a noticeable decay in signal quality. If other explanations for the decay are eliminated, then the practitioner may infer that a clot is forming. The hemodynamic signal also provides an early warning for arrhythmias. More specifically, the practitioner will observe an almost immediate change in hemodynamic signal during the onset of atrial fibrillation, bradycardia, or tachycardia. Once warned about onset of arrhythmia, the practitioner can provide appropriate treatments to the patient.

The pressure sensor 50a may have numerous functional elements and configurations, including optical sensors, mechanical sensors, micro-electrical-mechanical (MEMs) sensors, and the like. The sensor 50a may be removable from the pressure port 42, thereby potentially allowing the sensor 50a to be reused even as the catheter connector conduit 36 is disposed of as medical waste. The pressure sensor 50a is intended to be in constant fluid communication with the fluid flow path set 16, or at least configured such that pressure measured by the pressure sensor 50a is essentially equivalent to fluid pressure in the fluid flow path set 16, even if there is no direct contact between patient fluid and the pressure sensor 50a. The pressure sensor 50a is configured with sufficient sensitivity to measure pressure at least within a range of between about 0 mm Hg and about 300 mm Hg. The pressure sensor 50a is also configured to withstand pressure in excess of 1200 psi (about 63,000 mm Hg) without damaging the pressure sensor 50a. In this way, pressurized fluid from the powered fluid injector 12 may pass through the fluid path set 16 without damaging the pressure sensor 50a, while the pressure sensor 50a remains in fluid communication or contact with the fluid in the catheter connector conduit 36 via the continuously-open pressure port 42. The pressure sensor 50a may be a disposable, one-time-use device or may be reusable, as discussed above, if contamination between the pressure sensor 50a and patient fluid is sufficiently limited or prevented by some means, such as by use of a protective membrane or similar structure.

The pressure sensor 50a is illustrated as being coupled to a control unit 90 via a hemodynamic signal cable 92. The control unit 90 may be a computer, external computer network, or dedicated analysis system for displaying and/or analyzing data recorded by the pressure sensor 50a. Exemplary data analysis and processing systems capable of providing necessary detailed analysis of the measured hemodynamic signal include, but are not limited to, Avanta™, Arterion™, Panel PC GUI, and software packages residing on an Angio Informatics PC, all of which are proprietary to Medrad, Inc., the assignee of the present application. Alternative hemodynamic monitoring and analysis systems, as are known in the art, may also be used to process and analyze hemodynamic signals provided by the pressure sensor 50a.

With reference to FIG. 1B, another embodiment of a pressure sensor 50b is shown associated with the fluid path set 16. For example, the pressure sensor 50b may be associated with the disposable catheter connector conduit 36. As illustrated, the catheter connector conduit 36 may be provided with opposed end connectors 54, 56 for establishing respective fluid connections between the stopcock valve 40 and the catheter (not shown). The pressure sensor 50b is disposed between the opposed end connectors 54, 56 and, as was the case with the pressure sensor 50a described previously, the pressure sensor 50b is a high pressure sensor adapted to withstand pressure in excess of 60,000 mm Hg.

As discussed further herein, a pressure transducer (not shown) is disposed within the tubing portion 44 of the catheter connector conduit 36. The pressure transducer may be an optical transducer, mechanical transducer, MEMs transducer, or any other electronic device or assembly for measuring changes in fluid pressure. As will be described in greater detail herein, the pressure sensor 50b, may further include an external signal detector or monitor 60 in wired or wireless connection with the pressure transducer (not shown) disposed within the disposable tubing portion 44 of the catheter connector conduit 36. The pressure transducer is configured to transmit measured hemodynamic signals to the external monitor 60. For example, the pressure transducer may include a wireless transmitter for transmission of measured hemodynamic signals to the external monitor 60. Other devices and structures for information connection between the pressure transducer and external monitor 60 may include, but are not limited to, wired connections, radio waves, and others, and these alternative modalities may also be used for establishing an information connection between the pressure transducer and the external monitor 60.

In summary, in the present embodiment, the pressure sensor 50b is intended to be used only once per patient, as the pressure transducer (not shown) will likely come into physical contact with the medium that is a part of a fluid column extending from the patient through a catheter (not shown) to the tubing portion 44 of the catheter connector conduit 36. Additionally, the external monitor 60 is generally adapted to acquire the measured hemodynamic signals from the pressure transducer and may optionally have its own hemodynamic signal analysis capability. For example, the external monitor 60 may be adapted to processes or analyze the hemodynamic signals by, for example, excluding pressure values that fall outside of normal human intra-vascular pressure range. Other capabilities of the external monitor 60 are described herein, and the external monitor 60 may further include a display capability to provide the user with certain information regarding the hemodynamic signals measured by the pressure transducer. After analyses/processing, the measured hemodynamic signals may be provided to the control unit 90 through a wired connection provided by the hemodynamic signal cable 92 or a wireless connection. As another alternative, the external monitor 60 may merely be used to collect and/or transfer the measured hemodynamic signals measured by the pressure transducer to a remote control unit, such as the control unit 90. The control unit 90 may be a computer, external computer network, or dedicated analysis system for displaying and/or analyzing data recorded by the pressure sensor 50b, and this control feature may reside, for example, in the control system for the fluid injector 12 shown in FIGS. 1A-1C, in one embodiment.

With reference to FIG. 1C, a portion of the fluid path set 16 is shown and illustrates another embodiment of the pressure sensor 50c disposed between the opposed end connectors 54, 56 of the catheter connector conduit 36. As was the case with the pressure sensor 50b described previously, the pressure sensor 50c is a high pressure sensor adapted to withstand pressure in excess of 60,000 mm Hg. The pressure sensor 50c may again be an optical sensor, mechanical sensor, or MEMs sensor as non-limiting examples. This embodiment illustrates a pressure transducer 52 of the pressure sensor 50c disposed within the catheter connector conduit 36. The pressure transducer 52 is disposed inline within the tubing element or portion 44 of the catheter connector conduit 36, and the pressure transducer 52 is suitable for use in connection with the pressure sensor 50b discussed above in connection with FIG. 1B. In this embodiment, the pressure transducer 52 is shown hardwired to the control unit 90 by the hemodynamic signal cable 92, which extends from the pressure transducer 52, through the tubing element or portion 44 of the catheter connector conduit 36, and outward from the catheter connector conduit 36 via a side port 58. The side port 58 may be, for example, provided on end connector 54 used to establish a fluid connection with the stopcock valve 40. In the embodiment of FIG. 1C, the cable 92 is depicted as extending through a portion of the fluid path set 16 and exiting the fluid path set 16 through side port 58. However, it is understood that the cable 44 may exit the fluid path set 16 at any position along the fluid path set 16, and even extend to the fluid control module 24.

Figure 2B:
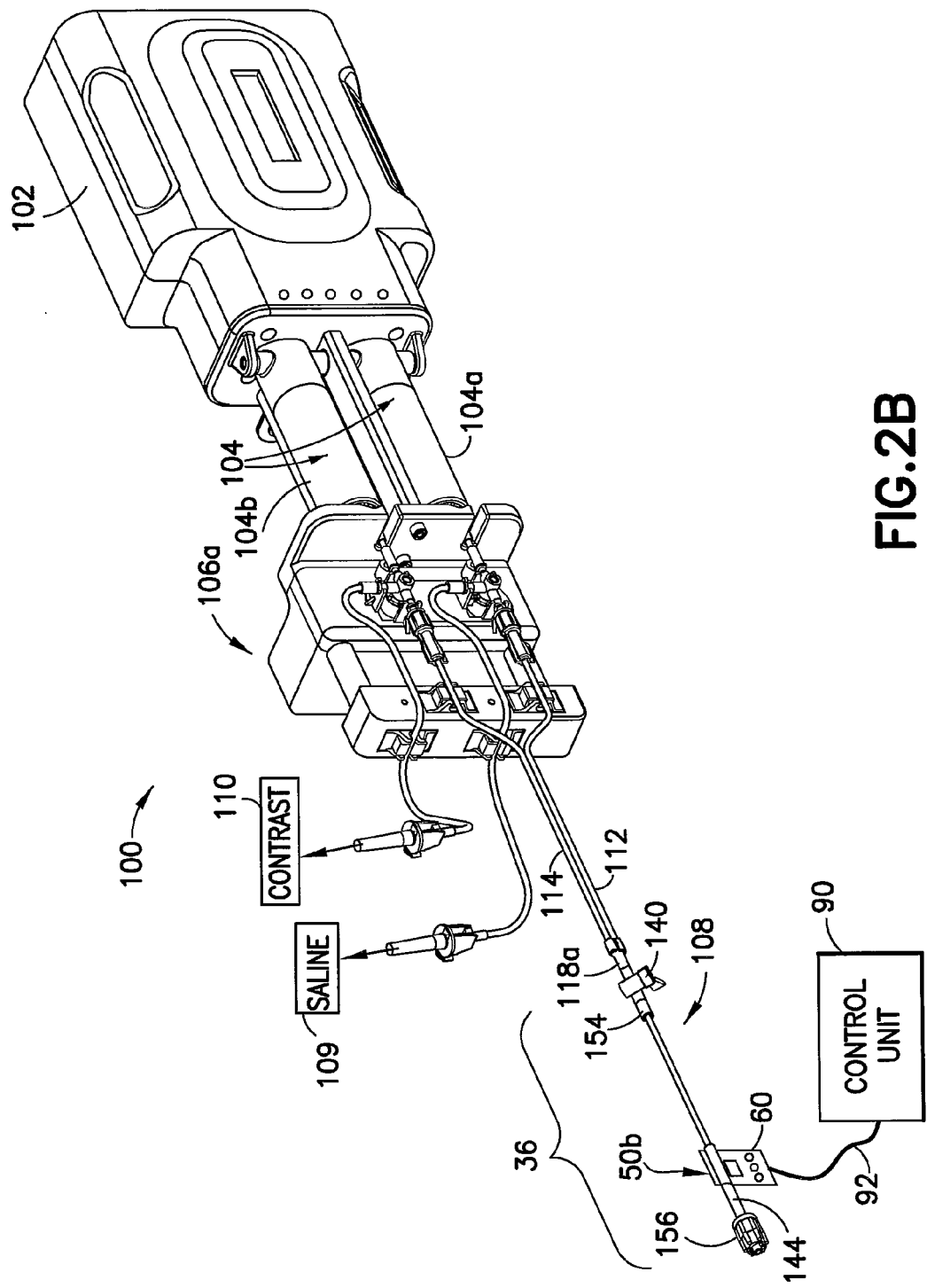
FIG. 2B is a perspective view of a fluid delivery system with a pressure sensor associated with a fluid path set according to another embodiment.

FIGS. 2A and 2B illustrate another embodiment of a fluid delivery system 100 having a powered fluid injector 102 adapted to accept and actuate a plurality of syringes, such as the two syringes 104 illustrated. The syringes 104 are fluidly connected to two (2) fluid sources, such as a source of saline 109 and a source of contrast media 110, or any two desired medical fluids. The fluid injector 102 is desirably at least a dual-syringe injector, wherein the two (2) fluid delivery syringes 104 are oriented in a side-by-side relationship and which are separately actuated by respective piston elements associated with the fluid injector 102. A fluid path set 108 may be interfaced with the syringes 104 associated with the fluid injector 102 in the fluid delivery system 100. In particular, the fluid injector 102 may include a fluid control module 106 that is generally adapted to support and interface the syringes 104 with the fluid path set 108; the fluid control module 106 may have control valves and like elements to control the fluid flow through the fluid path set 108 connected to the syringes 104. A suitable multi-syringe fluid injector for use with the above-described system is described in U.S. patent application Ser. No. 13/386,765, filed on Jan. 24, 2012, which published as U.S. Patent Application Publication No. 2012/0123257, and is assigned to the assignee of the present application, the disclosure of which is incorporated herein by reference in its entirety. Other relevant multi-fluid delivery systems are disclosed in U.S. patent application Ser. No. 10/159,592, filed on May 30, 2002 (published as U.S. 2004/0064041), and U.S. patent application Ser. No. 10/722,370, filed Nov. 25, 2003 (published as U.S. 2005/0113754), each of which are assigned to the assignee of the present application and the disclosures of which are incorporated herein by reference in their entireties.

The fluid path set 108 may have single and multi-use disposable sections in a similar manner to the fluid path set 16 described previously. The fluid path set 108 includes a first input line 112 in selective fluid communication with a first syringe 104a, a second input line 114 in selective fluid communication with a second syringe 104b, a downstream Y-connector 118 joining the first and second input lines 112, 114, and a catheter connector conduit 136. The catheter connector conduit 136 is again a disposable tubing section that connects the fluid path set 108 to a catheter (not shown) that is inserted within a patient for supplying the fluids from the saline source 109 and the contrast media source 110 to the patient. Desirably, the catheter connector conduit 136 is removably connected by a suitable connector 138 to a stopcock valve 140 that is provided between the Y-connector and the catheter connector conduit 136. The stopcock valve 140 may form a break point between reusable components of the fluid path set 108 and the disposable catheter connector conduit 136 in one embodiment. This configuration permits a user to isolate the reusable upstream components of the fluid path set 108 so that, when the stopcock valve 140 is in a closed position, a user can remove and replace the catheter connector conduit 136, and so that the multi-patient section of the fluid delivery system 100 can be used by another patient. The stopcock 140 is merely an exemplary structure for isolating the upstream components from the catheter connector conduit 136 and may be replaced by any suitable aseptic connector structure, but the stopcock 140 has the advantage of being manually actuated.

As in the embodiment of FIG. 1A, the embodiment of FIG. 2A includes a pressure port 142, but now positioned further downstream from the stopcock valve 140 and the Y-connector 118. Thus, the pressure port 142 is now shown as a branch port or element on a tubing portion 144 of the catheter connector conduit 136. In the present embodiment, the same pressure sensor 50a according to the embodiment illustrated in FIG. 1A is removably coupled to the pressure port 142. The removable pressure sensor 50a, as noted previously, is a high pressure sensor which is configured to have good sensitivity at pressures within the range of human intravascular pressure, but which also withstands fluid pressures in excess of 60,000 mm Hg. The pressure sensor 50a may again be connected to the control unit 90 through the hemodynamic signal cable 92 or may be wirelessly coupled to the control unit 90.

With reference to FIG. 2B, another embodiment of the fluid delivery system 100 is shown, which is similar to the fluid delivery system 10 of FIG. 1B. In FIG. 2B, the pressure sensor 50b is shown associated with the fluid path set 108. In particular, the pressure sensor 50b is shown associated with the disposable catheter connector conduit 136, which further comprises opposed end connectors 154, 156 for establishing respective fluid connections between the stopcock valve 140 and a catheter (not shown). The pressure sensor 50b is disposed between the opposed end connectors 54, 56 and, as was the case with the pressure sensor 50a described previously, the pressure sensor 50b is a high pressure sensor adapted to withstand pressure in excess of 60,000 mm Hg. As discussed briefly in connection with FIG. 1C and in further detail herein, a pressure transducer (not shown) is disposed within the tubing portion 144 of the catheter connector conduit 36. The pressure transducer may be an optical transducer, mechanical transducer, MEMs transducer, or any other electronic device or assembly for measuring changes in fluid pressure. As will be described in greater detail herein, the pressure sensor 50b may further include, or be connected to, an external signal detector or monitor 60 in wired or wireless connection with the pressure transducer (not shown) disposed within the disposable tubing portion 144 of the catheter connector conduit 136. As with the embodiment of the fluid delivery system 10 of FIG. 1B, the external detector or monitor 60 may be configured to process and analyze hemodynamic signals measured by the pressure transducer, or the external detector or monitor 60 may simply be used to collect and transfer the measured hemodynamic signals measured by the pressure transducer to a remote control unit, such as the control unit 90. The control unit 90 may be a computer, external computer network, or dedicated analysis system for displaying and/or analyzing data recorded by the pressure sensor 50b, and this control feature may reside, for example, in the control system for the fluid injector 102 shown in FIGS. 2A-2B, in one embodiment. The connection between the pressure transducer (not shown) and the external monitor detector 60 may be a wireless or wired connection.

Figure 3A:
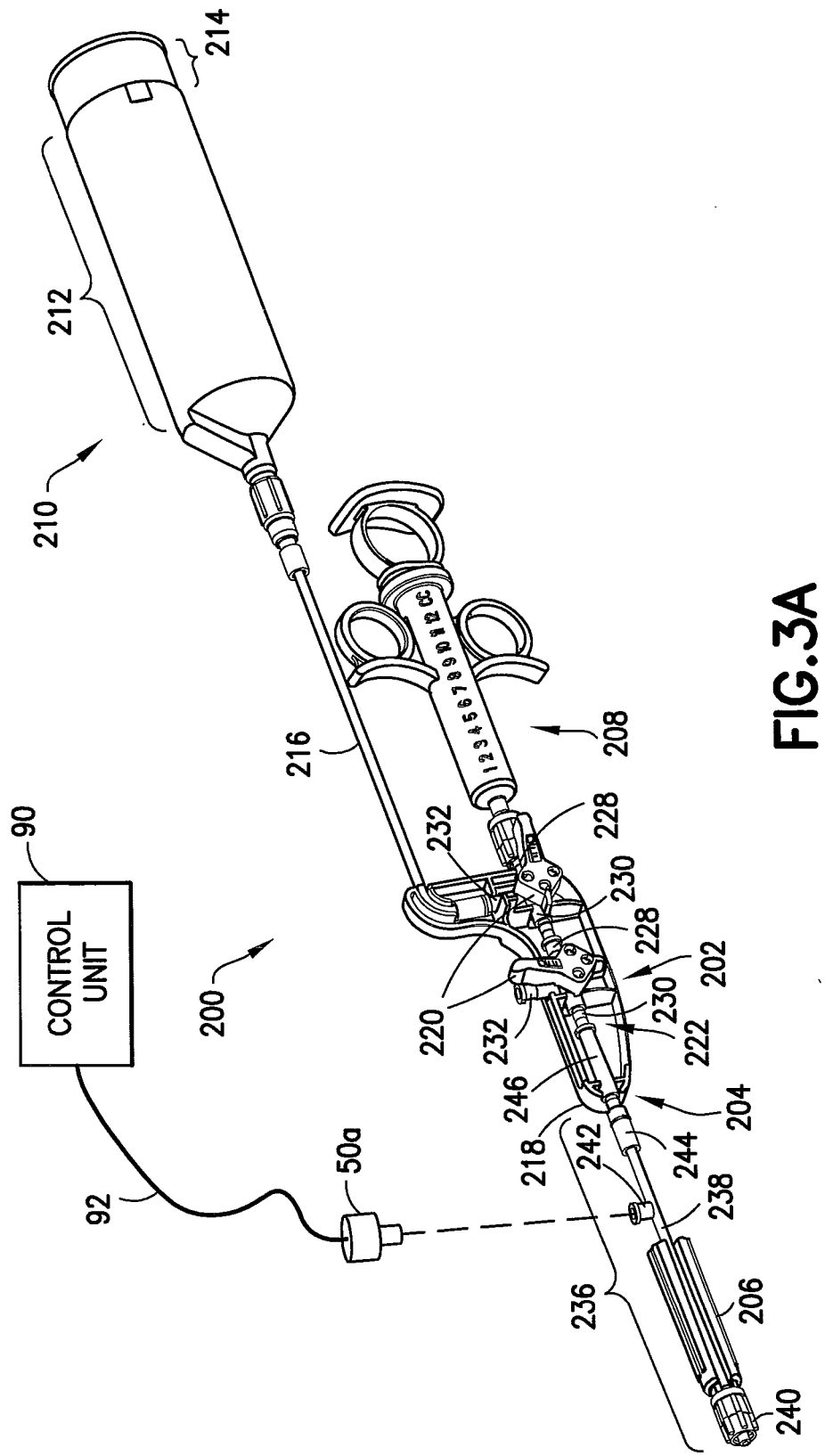
FIG. 3A is a perspective view of a fluid delivery system including a hand manifold and removable pressure sensor, according to one embodiment.
Figure 3B:
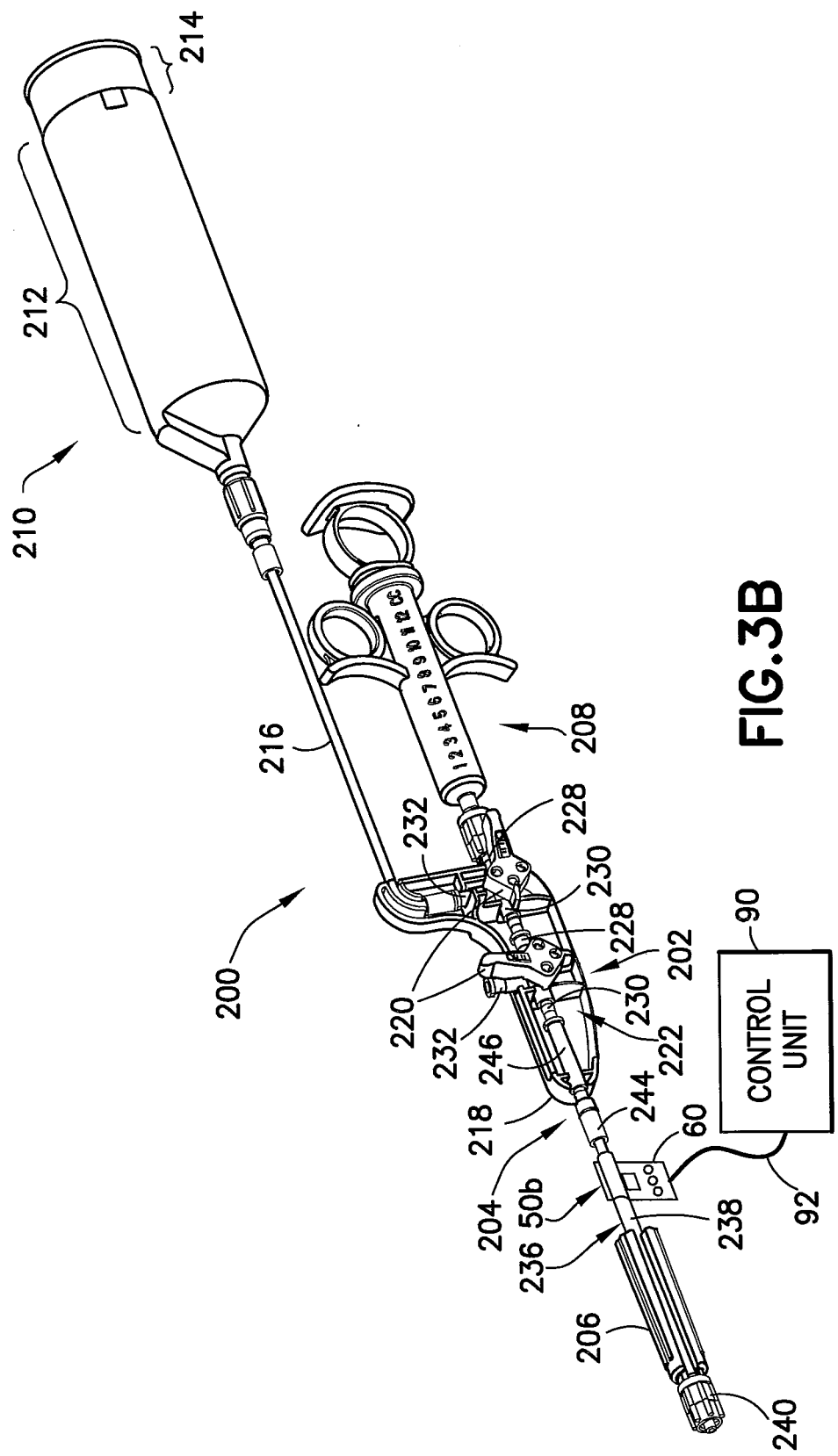
FIG. 3B is a perspective view of a fluid delivery system including a hand manifold and pressure sensor according to another embodiment.

With reference to FIGS. 3A and 3B, a further embodiment of a fluid delivery system 200 is shown and includes a hand-operated manifold 202 adapted for fluid connection to a plurality of fluid sources. An exemplary hand manifold for the hand-operated manifold 202 is disclosed in U.S. patent application Ser. No. 13/755,883, filed Jan. 31, 2013, assigned to the assignee of the present application, the disclosure of which is incorporated herein by reference. The fluid delivery system 200 may be connected to a patient connector fluid path set 204 having an optional tube stabilizer 206. The fluid sources may include a low pressure, hand operated syringe 208 and a high pressure syringe 210 adapted for mechanical interface with and actuation by a powered fluid injector (not shown). A suitable high pressure syringe 210 adapted to interface with a powered fluid injector may be found in United States Patent Application Publication No. 2009/0216192 to Schriver, et al. The high pressure syringe 210 generally comprises an elongated, cylindrical syringe body 212 defining an expansion section 214 at the open proximal end. Tubing 216 extends from the high pressure syringe 210 to the hand manifold 202.

The hand manifold 202 includes a manifold housing 218 formed to support a plurality of fluid control valves 220 that are connected in series with one another. The manifold housing 218 is generally L-shaped and defines a pocket 222 adapted to accept and support the fluid control valves 220. As shown in FIGS. 3A and 3B, each fluid control valve 220 includes at least a first port 228, a second port 230, and a third port 232. For the first fluid control valve 220, the first port 228 is connected to the low pressure syringe 208, the second port 230 is the outflow port, and the third port 230 is fluidly connected to the high pressure syringe 210. The second fluid control valve 220 is adapted to connect the first fluid control valve 220 with a catheter connector conduit 236 having a similar configuration to previous embodiments of the catheter connector conduit 36, 136. The catheter connector conduit 236 comprises a tubing portion or element 238 having a distal connector 240 for connection to a catheter (not shown). In the embodiment of FIG. 3A, the catheter connector conduit 236 includes a pressure port 242. The catheter connector conduit 236 further comprises a proximal end connector 244. For the second fluid control valve 220, the first port 228 is fluidly connected to the outflow or second port 230 of the first fluid control valve 220, the second port 230 is removably connected to the proximal end connector 244 via a suitable connector element 246, and the third port 232 is available for connection to another fluid source (not shown) such as a source of saline. Thus, the manifold 202 is arranged so that fluid passes from the second port 230 of the first fluid control valve 220 to the first port 228 of the second fluid control valve 220.

As shown in FIG. 3A, in the present embodiment, the same pressure sensor 50a according to the embodiment illustrated in FIGS. 1A and 2A is removably coupled to the pressure port 242. The removable pressure sensor 50a, as noted previously, is a high pressure sensor which is configured to have good sensitivity at pressures within the range of human intra-vascular pressure, but which also withstands fluid pressures in excess of 60,000 mm Hg. The pressure sensor 50a may again be connected to the control unit 90 through the hemodynamic signal cable 92 or may be wirelessly coupled to the control unit 90.

With reference to FIG. 3B, the pressure sensor 50b discussed previously may be associated with the catheter connector conduit 236. In FIG. 3B, the pressure sensor 50b is shown associated with the fluid path set 204. In particular, the pressure sensor 50b is shown associated with the disposable catheter connector conduit 236. The pressure sensor 50b is disposed between the opposed end connectors 244, 246 and adjacent the tube stabilizer 206. The pressure sensor 50b is again a high pressure sensor adapted to withstand pressure in excess of 60,000 mm Hg. As discussed briefly in connection with FIG. 1C and in further detail herein, a pressure transducer (not shown) is disposed within the tubing portion 238 of the catheter connector conduit 236. The pressure transducer may be an optical transducer, mechanical transducer, MEMs transducer, or any other electronic device or assembly for measuring changes in fluid pressure. As will be described in greater detail herein, the pressure sensor 50b, may further include, or be connected to, an external signal detector or monitor 60 in wired or wireless connection with the pressure transducer (not shown) disposed within the disposable tubing portion 238 of the catheter connector conduit 236. As with the embodiment of the fluid delivery system 10 of FIG. 1B and the fluid delivery system 100 of FIG. 2B, the external detector or monitor 60 may be configured to process and analyze hemodynamic signals measured by the pressure transducer, or the external detector or monitor 60 may simply collect and relay the hemodynamic signals measured by the pressure transducer to a remote control unit, such as the control unit 90. The control unit 90 may be a computer, external computer network, or dedicated analysis system for displaying and/or analyzing data recorded by the pressure sensor 50b, and this control feature may reside, for example, in the control system for the fluid injector 102 operating the high pressure syringe 210 shown in FIGS. 3A-3B, in one embodiment. The connection between the pressure transducer (not shown) and the external monitor detector 60 may be a wireless or wired connection.

Figure 4:
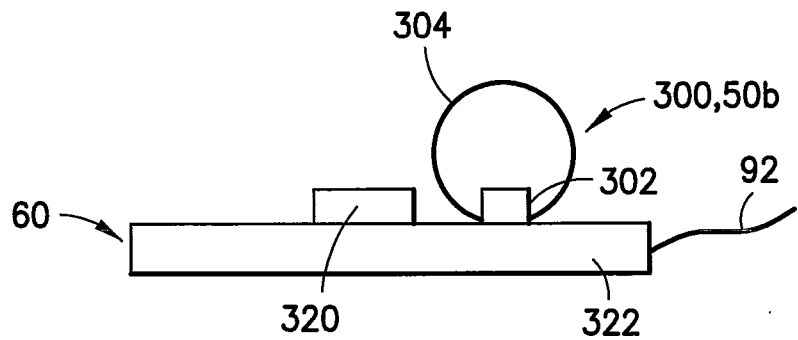
FIG. 4 is a schematic view of a pressure sensor for use in a fluid injection system, according to an embodiment of this disclosure.
Figure 5:
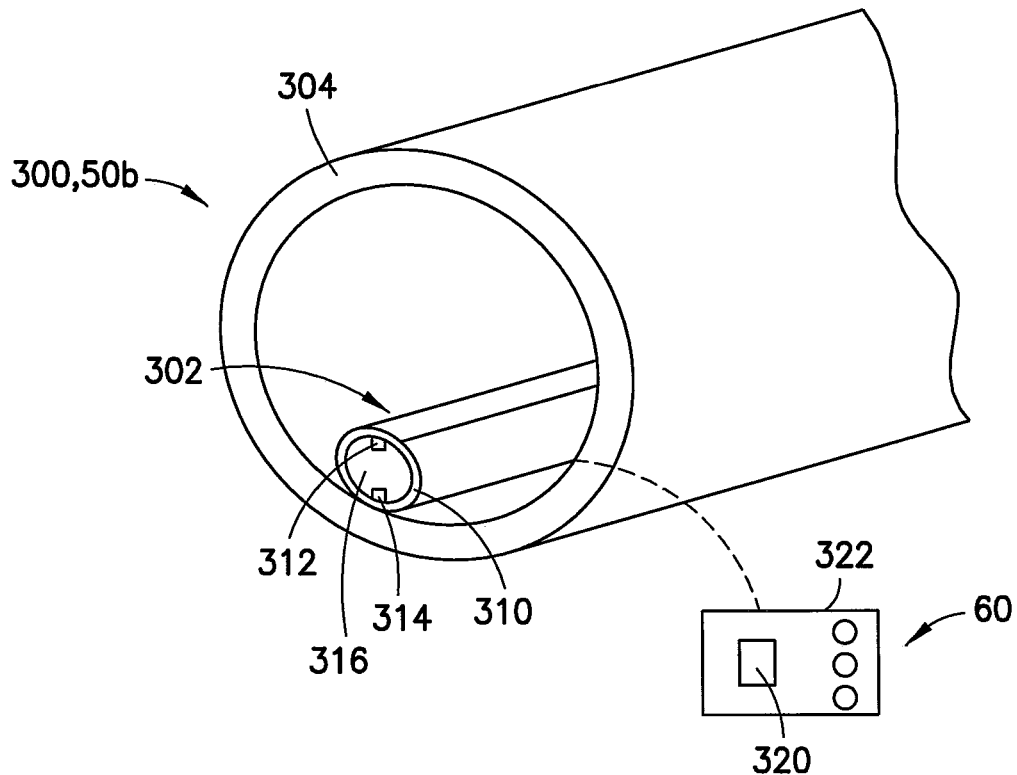
FIG. 5 is a perspective view of an optical pressure sensor according to an embodiment of this disclosure.
Figure 6:
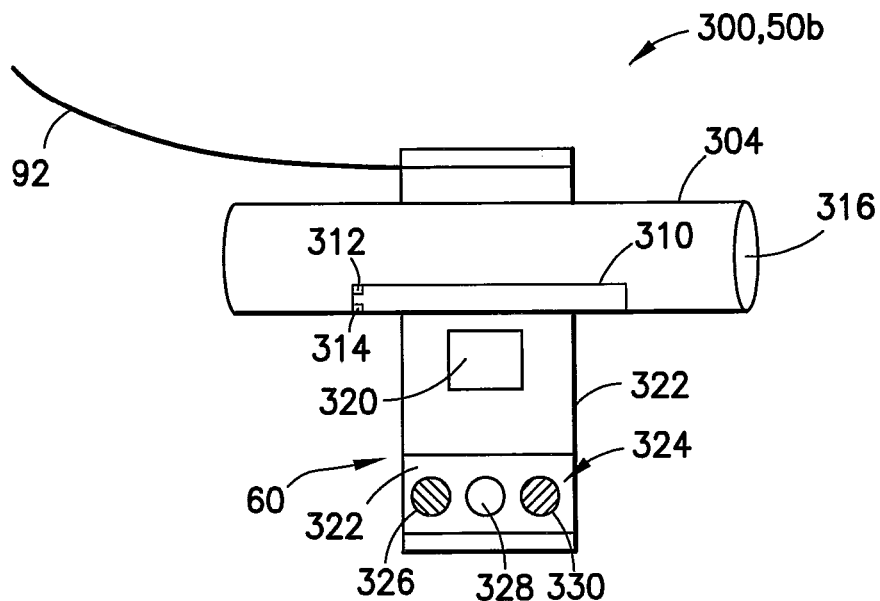
FIG. 6 is a partial perspective view of a pressure sensor including an external detector or monitor according to an embodiment of this disclosure.

Having described a number of exemplary embodiments of fluid delivery systems 10, 100, and 200, various exemplary embodiments of the pressure sensors 50a, 50b, 50c and associated control units will now be described. With reference to FIGS. 4-6, an embodiment of an in-line pressure sensor 300 that may be used as the pressure sensor 50b in the embodiments, described previously, is shown. The pressure sensor 300 includes an electronic pressure transducer 302 enclosed within a disposable tube 304. The disposable tube 304 may be any of the disposable tubing elements or portions 44, 144, or 238 depicted in FIGS. 1B, 2B, and 3B, respectively. Thus, the disposable tube 304 is a generic representation of the foregoing tubing elements or portions 44, 144, or 238 forming part of the catheter connector conduit 36 shown in FIG. 1B, the catheter connector conduit 136 shown in FIG. 2B, or the catheter connector conduit 236 shown in FIG. 3B. The disposable tube 304 is intended to be representative of any tubing element or section wherein it is desired to obtain hemodynamic pressure readings from a patient. The pressure transducer 302 is in informational electronic connection with an external detector or monitor 60. As described above in connection with the previously described embodiments, the connection may be any wired or wireless connection as is known in the art. In certain embodiments, the transmitted signal may be received by a signal processor 320 included within the external detector or monitor 60. The signal may be delivered from the external detector or monitor 60 to an external source through a standard interface cable 92, as described previously.

The signal processor 320 is configured to receive the hemodynamic signals measured by the pressure transducer 302 and to selectively transmit the signals to an external source such as an external control unit, computer, portable electronic device, or other dedicated electronic device for receiving, displaying, and analyzing the measured signals. The signal processor 320 may be configured to analyze data received from the pressure transducer 302 and to selectively exclude irrelevant data. For example, pressure readings that are orders of magnitude above typical intra-coronary pressures may be assumed to be incorrect or caused by fluid injection through the fluid path. The signal analysis processor 320 may be configured to exclude such readings rather than transferring such readings to the control unit 90.

With specific reference to FIG. 5, in one embodiment, the pressure sensor 300 is an optical sensor which further includes an inner tube 310 provided within the disposable tube 304. The inner tube 310 is formed from a flexible material, such that the tube 310 deforms in response to increasing fluid pressure in the disposable tube 304. The pressure transducer 302 is configured to measure deformation of the inner tube 310 and includes a radiation generator 312 and receiver 314 disposed within the deformable inner tube 310. The radiation generator 312 is configured to promulgate a radiation beam through the inner tube 310, allowing the beam to reflect from an interior surface 316 of the inner tube 310. The reflected radiation wave is received by the receiver 314, which may be integral with the radiation generator 312 or may be a separate receiving element. As fluid pressure increases, the inner tube, or deformable element 310 deforms altering the reflection angle, phase, or period duration of the reflected beam. Variations in the reflected beam are monitored by the signal processor 320 or control unit 90 and used to determine the amount of deformation of the deformable inner tube 310. Deformation of the inner tube 310 corresponds to the fluid pressure in the disposable tube 304. Pressure sensors 300 having different configurations may also be used. For example, an optical sensor may be projected on a deformable diaphragm or other deformable structure may be used in the disposable tube 304 to measure fluid pressure, such as the embodiment described in connection with FIGS. 8A-8C described herein.

With further reference to FIG. 6, in one embodiment, the signal measured by the pressure transducer 302 is delivered to the external detector 60 and the signal processor 320 for analysis. Signal analysis performed by the signal processor 320 can be delivered to a user (e.g., physician and clinical staff) in multiple ways. In the simplest form, the analyzed signal itself is provided on monitoring equipment already available in typical Interventional Radiology and Cardiology suites. Similarly, the signal can be displayed on an overhead monitor. Alternatively, the hemodynamic waveform can be provided on a computer monitor dedicated for that purpose, to provide an increased level of analysis for a user. The increased analysis and multiple viewing locations reduces the need for constant monitoring of the hemodynamic signal, provides visual feedback about the condition of the patient and operation of the fluid delivery system, and may provide for simultaneous automated backup of recorded data.

In certain embodiments, the signal processor 320 may also be configured to determine information about the fluid delivery system 10, 100, 200, including whether the fluid delivery system 10, 100, 200 is connected to a patient, whether the system is ready for use, and whether a fluid injection can safely be performed. For example, the signal process 320 may be configured to compare a hemodynamic pressure signal measured by the pressure sensor 300 with an expected pressure value, such as an expected pressure value when a specific fluid volume is injected through the fluid delivery system 10, 100, 200. If the pressure measured by the pressure sensor 300 is less than the expected pressure value, the signal processor 320 determines that air may be present in the fluid line. Accordingly, the fluid line must be purged to remove air bubbles before using the fluid delivery system 10, 100, 200 to inject fluid into a patient. Similarly, in a further non-limiting embodiment, the signal processor 320 may be configured to predict the size of air bubbles present in a fluid line by comparing the measured pressure (e.g., the measured systolic and diastolic pressures) provided by the pressure sensor 300, according to a predetermined algorithm for comparing measured and expected pressure values. Similarly, when measured pressure indicates that the fluid delivery system 10, 100, 200 is connected to a patient, the signal processor 320 may prevent a user from purging air through the system. If necessary, the signal processor 320 may also trigger an audible or visual alarm to alert a user about certain dangerous situations.

In certain further embodiments, the pressure sensor 300 may be configured to provide a user, such as a clinician or practitioner, with data related to fluid flow through the fluid delivery system 10, 100, 200 and patient intravascular pressure data directly on the pressure sensor 300 itself. As mentioned previously, fluid pressure may fall outside of the normal intracoronary range for a number of reasons, such as when a thrombosis is forming in close proximity to the catheter, or when onset of arrhythmia is imminent. As an example, if abnormal intracoronary pressure is observed, a practitioner would likely want to perform additional evaluation of the fluid path and/or patient before using the fluid delivery device to inject fluid into the patient.

Accordingly, in an exemplary embodiment shown in FIG. 6, the external detector or monitor 60 includes a visual display 322, for example having one or more visual indicators 324 configured to provide relevant information about the condition of the patient and/or a fluid path, such as fluid pressure in the fluid path. In the present disclosure, such a fluid path may include, for example, such as the fluid pressure within tubing elements or portions 44, 144, or 238 forming part of the catheter connector conduit 36 shown in FIG. 1B, the catheter connector conduit 136 shown in FIG. 2B, or the catheter connector conduit 236 shown in FIG. 3B, particularly whether the measured pressure is within a normal range. The visual indicators 324 may include, as an example, a series of colored light emitting diodes (LEDs) arranged on the housing of the external detector or monitor 60, a button or features on a small user interactive display, and like devices. In one embodiment, a warning indicator 326, which may be a red LED, indicates that the waveform currently being observed is outside the bounds of normal human intra-coronary pressure. Examples of reasons why such a reading is received include that the patient's heart rate is above 220 beats per minute, that no heart rate is observed, or that a waveform is so dampened that it could not signify heart function. A caution indicator 328 may indicate that the waveform being observed is within a possible human range, but outside of the normal range for a patient. Examples of reasons for such a reading include occurrence of a change to systolic or diastolic pressures, loss of signal properties from the pressure sensor 300, or signal properties that indicate boundary conditions of the catheter. A ready-for-use indicator 330, possibly signified by a green LED, may signal that the waveform currently being monitored is typical for patients. It is noted that a green indicator may not be an indication that a patient is in good health, but merely an indication of good hemodynamic signal. While the visual indicators 324 are depicted as being positioned on the visual display 322 of the external detector or monitor 60, it will also be understood that the visual indicators 324 may be positioned at other locations within the scope of this disclosure. For example, the visual indicators 324 may be on the control unit 90 or some other external device. The visual indicators 324 may also be displayed on a computer monitor or other existing display unit already present in an operating room or imaging/cardiac suite.

Figure 7:
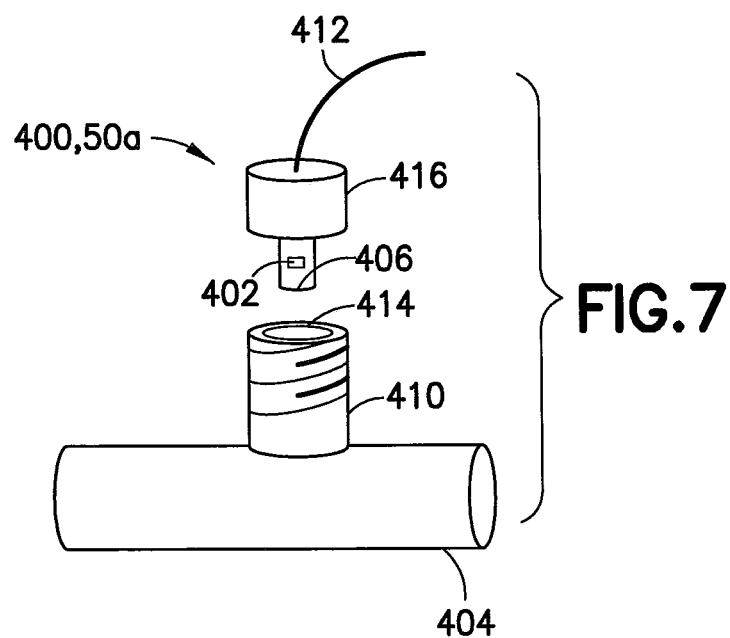
FIG. 7 is a perspective schematic view of a fluid tubing element and a removable pressure sensor according to an embodiment of this disclosure.

With reference to FIG. 7, a pressure sensor 400 is depicted that may be used as the pressure sensor 50a in the embodiments described previously is shown. The pressure sensor 400 is configured to be removably inserted in a pressure port 410 such as the pressure ports 42, 142, and 242 depicted in FIGS. 1A, 2A, and 3A, respectively. The pressure sensor 400 includes a pressure transducer 402. A hemodynamic interface cable 412 is connected to the pressure sensor 400. The interface cable 412 extends to the control unit 90, discussed previously, such as a computer, handheld computer, or dedicated monitoring and analysis device. The pressure sensor 400 may be a reusable sensor, which can be used in fluid path sets for different patients rather than being disposed of following each use. In this case, the pressure sensor 400 and/or pressure port 410 may be lined with a protective material 414 to prevent direct contact between patient fluid contained in a fluid tubing path 404, such as tubing elements or portions 44, 144, or 238, and the pressure sensor 400. The pressure sensor 400 may further include a deformable diaphragm or element 406 that flexes in response to fluid pressure from the fluid delivery system 10, 100, 200. The pressure transducer 402, such as an optical transducer, mechanical transducer, or MEMs transducer may be used to measure the deformation of the diaphragm 406. In certain embodiments, the diaphragm 406 is anchored to a sensor housing 416.

Figure 8A:
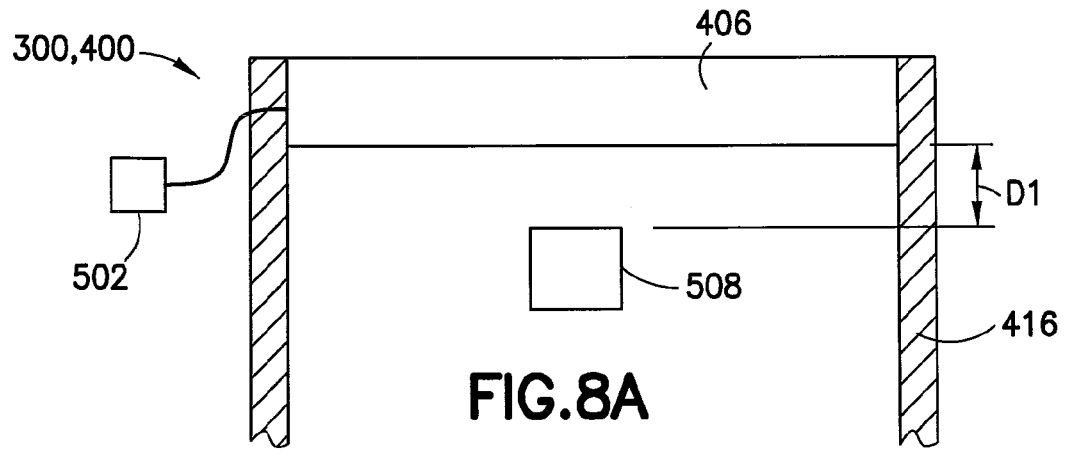
FIGS. 8A-8C are schematic views of a micro-electro-mechanical (MEMs) pressure sensor according to an embodiment of this disclosure.
Figure 8B:
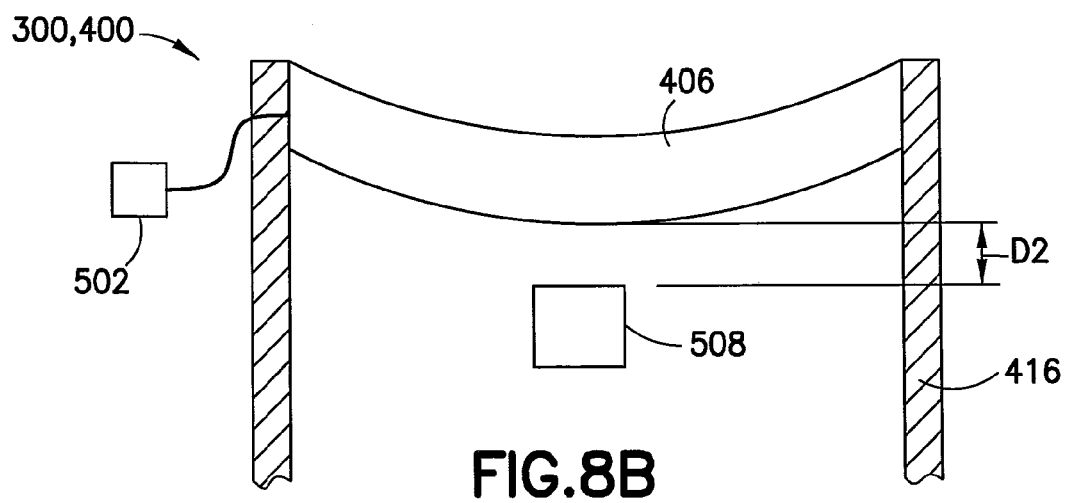
Figure 8C:
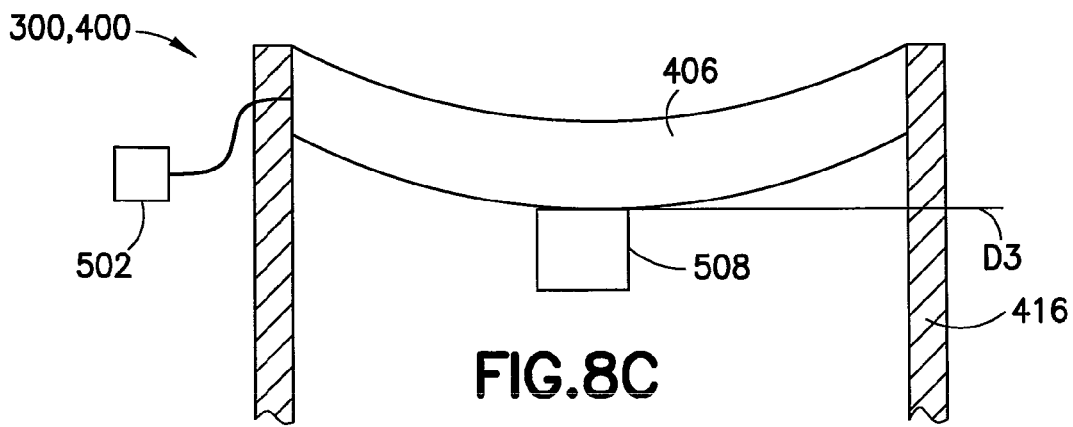

With reference to FIGS. 8A-8C, the pressure sensors 300, 400 may be provided with a micro-electro-mechanical (MEMs) based electronic pressure transducer 502. The following discussion of the MEMs based electronic pressure transducer 502 proceeds in the context of the pressure sensor 400 for expediency in explaining the operational features of FIGS. 8A-8C, but this specific context should not be deemed as limiting, and are applicable to, for example, the pressure sensor 50b described previously. Thus, the concepts described in connection with FIGS. 8A-8C may be applied with respect to pressure sensor 300 and, thus, pressure sensor 50b described above. In FIGS. 8A-8C, the MEMs based electronic pressure transducer 502 measures deformation of the flexible diaphragm 406. As external fluid pressure increases, the flex or deformation of the diaphragm 406 proportionally increases. The pressure transducer 502 includes electronic components (not shown) to convert to an electronic signal a representation of the amount of the deflection or deformation of the diaphragm 406; such a deflection or deformation and measurement thereof is analogous to measurements taken using strain gauges. As described above, with previously known mechanical pressure transducers, substantial increases in pressure damages the mechanical pressure transducers rendering the pressure sensor unusable. To address this problem, the pressure sensors 300, 400 further includes a guard 508 or backstop to prevent the diaphragm 406 from deforming far enough to cause irreversible damage to the pressure transducer 502. The guard 508 is configured to engage and counteract deformation of the diaphragm 406 when pressure exceeds a predetermined value. The diaphragm 406 remains engaged to the guard 508 until the fluid pressure decreases below the predetermined value.

More specifically, as shown in FIG. 8A, when no fluid pressure is present (P=0 mm Hg), the diaphragm 406 is free from biasing force and a gap of distance D1 exists between the diaphragm 406 and guard 508. As pressure increases, the diaphragm 406 deforms reducing the distance D2 between the diaphragm 406 and guard 508. When pressure exceeds the desired monitoring range (e.g., a range of possible human intracoronary pressure) the diaphragm 406 contacts the guard 508, meaning that the distance D3 between the diaphragm 406 and guard 508 is 0. It is noted that, in this configuration, the pressure sensor 400 cannot provide a pressure reading after the diaphragm 406 engages the guard 508, or exhibits a maximum reading. In certain embodiments, the pressure sensor 400 may then produce an indication that pressure is unreadable or indeterminable. The pressure sensor 400 becomes operational again once pressure decreases to within the predetermined range.

While specific embodiments of the high pressure sensor for a fluid delivery system having been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of invention which is to be given the full breadth of the claims appended and any and all equivalents thereof.

The invention claimed is:

1. A hemodynamic pressure sensor for use with a fluid delivery system, the hemodynamic pressure sensor comprising:
   a fluid path defined by a tubing element; and
   a pressure transducer configured to be in continuous fluid communication with a fluid in the tubing element during pressurized delivery of the fluid and adapted to measure a fluid pressure in the tubing element, the pressure transducer comprising a deformable element configured to deform in response to changes in the fluid pressure in the tubing element,
   wherein the pressure transducer converts to an electronic signal a representation of an amount of deformation of the deformable element to measure the changes in the fluid pressure in the tubing element, and
   wherein the deformable element of the pressure transducer is configured such that it remains in working condition after being exposed to pressure in excess of about 60,000 mm Hg.

2. The hemodynamic pressure sensor of claim 1, wherein the pressure transducer is configured to measure the fluid pressure within the range of between about 0 mm Hg to about 300 mm Hg.

3. The hemodynamic pressure sensor of claim 1, wherein the pressure transducer is configured to be placed in fluid connection with a pressure port in fluid communication with the tubing element, and
   wherein the fluid with the fluid pressure to be measured by the pressure transducer enters the pressure port.

4. The hemodynamic pressure sensor of claim 1, wherein the pressure transducer is an optical pressure transducer and the deformable element is a flexible tube enclosing the optical pressure transducer.

5. The hemodynamic pressure sensor of claim 4, wherein the pressure transducer further comprises:
   a radiation generator for promulgating a radiation beam through the flexible tube; and
   a detector for detecting the promulgated radiation beam,
   wherein the flexible tube is configured to deform in response to the changes in the fluid pressure in the tubing element,
   wherein the flexible tube is oriented in a direction of a fluid flow, and wherein the pressure transducer is configured to measure the deformation of the flexible tube.

6. The hemodynamic pressure sensor of claim 1, wherein the deformable element is a diaphragm which flexes in response to the changes in the fluid pressure within the tubing element and wherein the pressure transducer measures flexing of the diaphragm and converts to an electronic signal a representation of the amount of the flexing of the diaphragm to measure the changes in the fluid pressure in the tubing element.

7. The hemodynamic pressure sensor of claim 6, further comprising a guard which selectively engages and restricts movement of the diaphragm.

8. The hemodynamic pressure transducer of claim 7, wherein the guard engages the diaphragm when the fluid pressure in the tubing element exceeds a possible human intra-coronary pressure range.

9. The hemodynamic pressure sensor of claim 1, further comprising an external monitor in electronic communication with the pressure transducer; and
 a visual display on the external monitor for displaying information based on the electronic signal to a user.

10. The hemodynamic pressure sensor of claim 9, wherein the external monitor comprises a signal analysis processor for receiving the electronic signal from the pressure transducer, wherein the signal analysis processor is adapted to process the electronic signal and transmit the electronic signal to a control unit.

11. The pressure sensor of claim 9, wherein the visual display comprises a visual indicator comprising at least:
 a warning indicator which informs the user when the measured fluid pressure is outside of a possible human intra-coronary pressure range;
 a caution indicator that informs the user when the measured fluid pressure is outside of a normal human intra-coronary pressure range, but within the possible human intra-coronary pressure range; and
 a ready-for-use indicator that indicates that the measured fluid pressure is within the normal human intra-coronary pressure range.

12. The pressure sensor of claim 1, wherein the pressure transducer is connected to an external monitor by one of a wired and a wireless connection.

13. A fluid delivery system comprising:
 a first fluid delivery device for delivering a first injection fluid under pressure to a fluid path defined by a tubing element;
 a second fluid delivery device for delivering a second injection fluid under pressure to the tubing element; and
 a pressure transducer configured to be in continuous fluid communication with a fluid in the tubing element during pressurized delivery of the fluid and adapted to measure a fluid pressure in the tubing element, the pressure transducer comprising a deformable element configured to deform in response to changes in the fluid pressure in the tubing element,
 wherein the pressure transducer converts to an electronic signal a representation of an amount of deformation of the deformable element to measure the changes in the fluid pressure in the tubing element, and
 wherein the deformable element of the pressure transducer is configured such that it remains in working condition after being exposed to pressure in excess of about 60,000 mm Hg.

14. The fluid delivery system of claim 13, further comprising a hand manifold comprising a plurality of fluid control valves in series fluid communication and connected to the first and the second fluid delivery devices and to the tubing element, the plurality of fluid control valves selectively permitting a fluid flow between the first and the second fluid delivery devices and the tubing element.

15. The fluid delivery system of claim 14, wherein the pressure transducer is configured to be placed in fluid connection with a pressure port in fluid communication with the tubing element; and
 wherein the fluid with the fluid pressure to be measured by the pressure transducer enters the pressure port.

16. The fluid delivery system of claim 13, wherein the pressure transducer is an optical pressure transducer and the deformable element is a flexible tube enclosing the optical pressure transducer.

17. The fluid delivery system of claim 16, wherein the pressure transducer further comprises:
 a radiation generator for promulgating a radiation beam through the flexible tube; and
 a detector for detecting the promulgated radiation beam, wherein the flexible tube is configured to deform in response to the changes in the fluid pressure in the tubing element,
 wherein the flexible tube is oriented in a direction of a fluid flow, and
 wherein the pressure transducer is configured to measure the deformation of the flexible tube.

18. The fluid delivery system of claim 13, wherein the deformable element is a diaphragm which flexes in response to the changes in the fluid pressure within the tubing element and wherein the pressure transducer measures flexing of the diaphragm and converts to an electronic signal a representation of the amount of the flexing of the diaphragm to measure the changes in the fluid pressure in the tubing element.

19. The fluid delivery system of claim 18, further comprising a guard which selectively engages and restricts movement of the diaphragm.

20. The hemodynamic pressure sensor of claim 1, further comprising an external monitor in electronic communication with the pressure transducer, wherein the external monitor comprises a signal analysis processor for receiving the electronic signal from the pressure transducer, wherein the signal analysis processor is adapted to process the electronic signal and transmit the electronic signal to a control unit.

21. A fluid delivery system, comprising:
 a power injector adapted to interface with and actuate at least one syringe;
 a fluid path set connected to the at least one syringe and comprising a tubing element; and
 a pressure transducer configured to be in continuous fluid communication with a fluid in the tubing element during pressurized delivery of the fluid and adapted to measure a fluid pressure in the tubing element, the pressure transducer comprising a deformable element configured to deform in response to changes in the fluid pressure in the tubing element;
 wherein the pressure transducer converts to an electronic signal a representation of an amount of deformation of the deformable element to measure the changes in the fluid pressure in the tubing element; and
 wherein the deformable element of the pressure transducer is configured such that it remains in working condition after being exposed to pressure in excess of about 60,000 mm Hg.

22. The fluid delivery system of claim 21, wherein the pressure transducer is configured to measure the fluid pressure within the range of between about 0 mm Hg to about 300 mm Hg.

23. The fluid delivery system of claim 21, wherein the pressure transducer is configured to be placed in fluid connection with a pressure port in fluid communication with the tubing element, and
wherein the fluid with the fluid pressure to be measured by the pressure transducer enters the pressure port.

24. The fluid delivery system of claim 21, wherein the pressure transducer is an optical pressure transducer and the deformable element is a flexible tube enclosing the optical pressure transducer.

25. The fluid delivery system of claim 24, wherein the pressure transducer further comprises:
a radiation generator for promulgating a radiation beam through the flexible tube; and
a detector for detecting the promulgated radiation beam,
wherein the flexible tube is configured to deform in response to the changes in the fluid pressure in the tubing element,
wherein the flexible tube is oriented in a direction of a fluid flow, and
wherein the pressure transducer is configured to measure the deformation of the flexible tube.

26. The fluid delivery system of claim 21, wherein the deformable element is a diaphragm which flexes in response to the changes in the fluid pressure within the tubing element and wherein the pressure transducer measures flexing of the diaphragm and converts to an electronic signal a representation of the amount of the flexing of the diaphragm to measure the changes in the fluid pressure in the tubing element.

27. The fluid delivery system of claim 26, further comprising a guard which selectively engages and restricts movement of the diaphragm.

28. The fluid delivery system of claim 21, further comprising:
an external monitor in electronic communication with the pressure transducer; and
a visual display on the external monitor for displaying the electronic signal to a user.

29. The fluid delivery system of claim 28, wherein the external monitor comprises a signal analysis processor for receiving the electronic signal from the pressure transducer, wherein the signal analysis processor is adapted to process the electronic signal and transmit the electronic signal to a control unit.

30. The hemodynamic pressure sensor of claim 1, wherein a fluid connection between the tubing element and the pressure transducer is free from a pressure isolation mechanism.

* * * * *

UNITED STATES PATENT AND TRADEMARK OFFICE
CERTIFICATE OF CORRECTION

PATENT NO.        : 9,486,579 B2
APPLICATION NO.   : 13/798709
DATED             : November 8, 2016
INVENTOR(S)       : Riley et al.

It is certified that error appears in the above-identified patent and that said Letters Patent is hereby corrected as shown below:

In the Specification
In Column 11, Line 12, delete "cable 44" and insert -- cable 92 --, therefor.
In Column 13, Line 29, delete "third port 230" and insert -- third port 232 --, therefor.

In the Claims
In Column 19, Line 14, in Claim 8, delete "transducer" and insert -- sensor --, therefor.
In Column 19, Line 29, in Claim 11, delete "The pressure sensor" and insert -- The hemodynamic pressure sensor --, therefor.
In Column 19, Line 41, in Claim 12, delete "The pressure sensor" and insert -- The hemodynamic pressure sensor --, therefor.

Signed and Sealed this
Eleventh Day of April, 2017

Michelle K. Lee
*Director of the United States Patent and Trademark Office*